United States Patent [19]
Salte et al.

[11] Patent Number: 4,960,795
[45] Date of Patent: Oct. 2, 1990

[54] FEED ADDITIVE AND FEED CONTAINING SUCH ADDITIVE

[75] Inventors: Ragnal Salte, Sogndal; Magny S. Thomassen, Oslo, both of Norway

[73] Assignee: Norsk Hydro a.s., Oslo, Norway

[21] Appl. No.: 276,854

[22] Filed: Nov. 28, 1988

[30] Foreign Application Priority Data

Dec. 21, 1987 [GB] United Kingdom ............... 8729751

[51] Int. Cl.$^5$ .................... A61K 31/20; A23K 1/00
[52] U.S. Cl. ........................................ 514/560; 426/2
[58] Field of Search .................. 514/560; 426/2, 643

[56] References Cited

U.S. PATENT DOCUMENTS 4,615,839 10/1986 Seto et al. ........................ 514/560

FOREIGN PATENT DOCUMENTS

| 222169 | 5/1987 | European Pat. Off. |
| 296751 | 12/1988 | European Pat. Off. ............ 514/560 |
| 1465276 | 2/1977 | United Kingdom . |
| 1604381 | 12/1981 | United Kingdom . |
| 1604382 | 12/1981 | United Kingdom . |
| 2090529 | 7/1982 | United Kingdom . |
| 2104907 | 3/1983 | United Kingdom . |
| 2134782 | 8/1984 | United Kingdom . |

OTHER PUBLICATIONS

Derwent Abstract of JP Patent No. 60-169418 (9/2/85).
Garrison et al., "The Nutrition Desk Reference" (1985), pp. 167–168.
Merck-Index, 1983, p. 510, Paragraph 3500.

Primary Examiner—Douglas W. Robinson
Assistant Examiner—Raymond J. Henley, III
Attorney, Agent, or Firm—Wenderoth, Lind & Ponack

[57] ABSTRACT n-3 Polyunsaturated fatty acids, or digestive derivatives thereof, are used to prevent or treat cold water diseases in farmed fish. Thus, incorporation of such fatty acids, preferably (all Z) 5, 8, 11, 14, 17 eicosapentaenoic acid and/or (all Z) 4, 7, 10, 13, 16, 19 docosahexaenoic acid, or digestive derivatives thereof, into the feed for Atlantic farmed salmon has been found. to significantly reduce the incidence of "Hitra" disease.

12 Claims, 1 Drawing Sheet

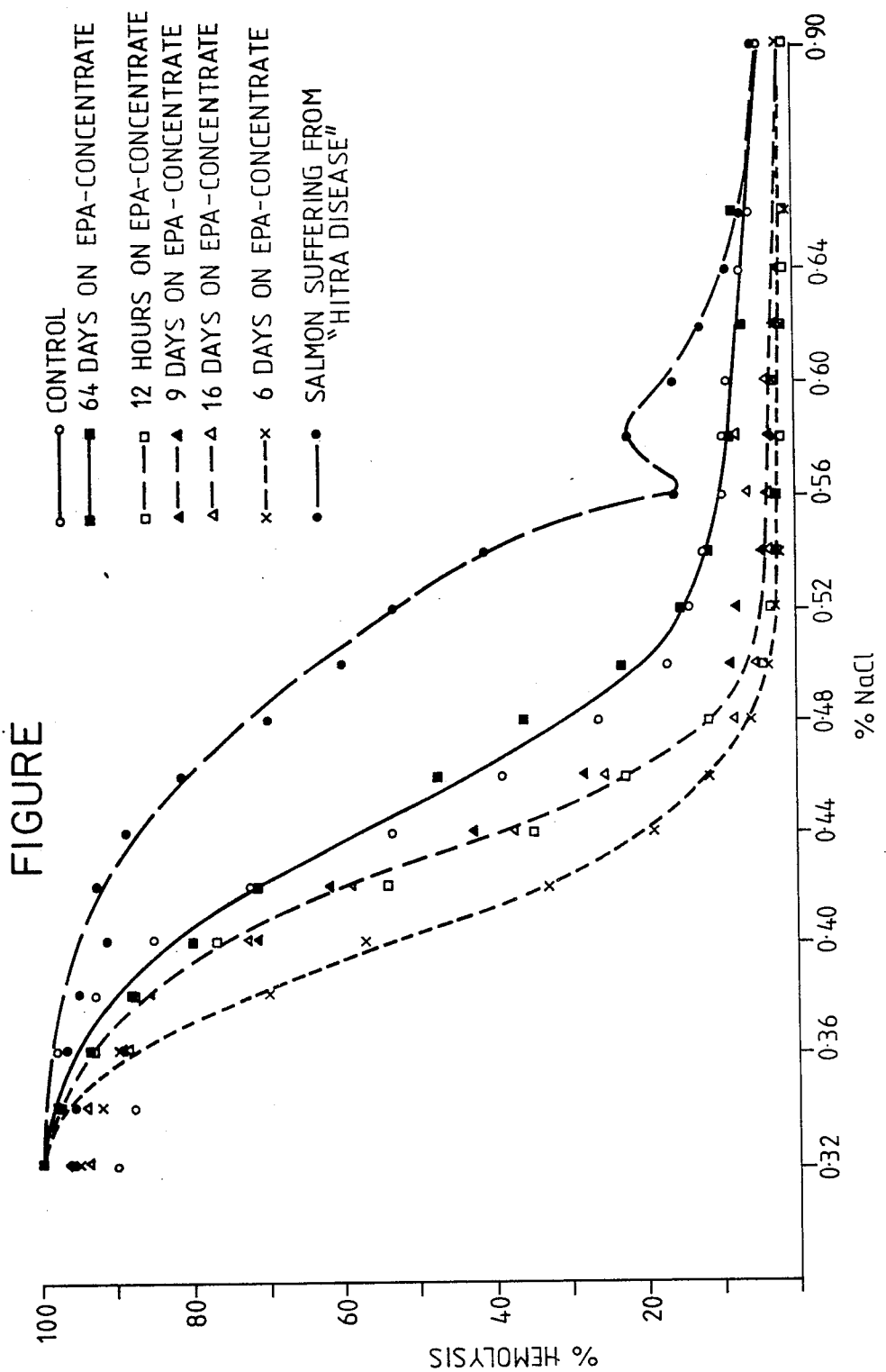

FEED ADDITIVE AND FEED CONTAINING SUCH ADDITIVE

This invention relates to a feed additive and a feed containing this feed additive, which can be used for prophylaxis and for the treatment of disease in farmed fish, especially for the prevention of disease in farmed Atlantic salmon at low water temperatures.

Since it was first recognized in 1977, "Hitra disease", or hemorrhagic syndrome, has been the most economically significant disease in Norwegian salmonid farming. The eponym "Hitra-disease" refers to the island where the disease first posed a major problem. The disease affects any age-class of fish in seawater and has a greater prevalence in winter. "Hitra-disease" is almost exclusively a disease in farmed Atlantic salmon (*Salmo salar L.*), although it is known to occur in rainbow trout (*Salmo gairdneri* Richardson). It has only been reported twice from outside of Norway, i.e., from Scotland and from the Faroe islands. A similar disease named "Bremnes disease" has caused considerable losses in Norwegian salmon farms during the last 2 years, and an apparent equivalent to this disease, "Salmon Plague", has also been reported from the Faroe islands.

"Hitra disease" is characterized by hemorrhages, edema and, in the terminal stage, by stupor and coma. The etiology is controversial. Necropsy findings in adult salmon with subclinical disease varied from negligible to hemorrhagic diathesis with generalized edema.

By light microscopy, minute vessels were dilated, arterioles had mural necrosis, and thrombi were present. Occlusions consisted of fused erythrocytes and fibrin. Ultrastructurally, endothelial nuclei were pyknotic with condensed chromatin. The cytoplasm contained numerous laminar structures and electron-dense particles. Damaged erythrocytes adhered to the degenerated endothelium, and coalesced erythrocytes had formed mural thrombi or filled the vascular lumen. Microthrombi were frequently seen. There were no thrombocytes in the thrombi, which consisted of erythrocytes or reticulocytes. Clinically healthy farmed salmon parr showed the same disorders as did adults, but to a far lesser degree. Wild salmon parr had normal microvasculature. Results indicated that disseminated intravascular coagulation (DIC) occurs in "Hitra disease" in farmed Atlantic salmon. R. Salte et al., Vet. Pathol., 378-385 (1987). This has later been confirmed by hematological studies.

The above observations were further reflected in the occurrence of intravascular coagulation, and in the reduced osmotic resistance of cells from salmon with subclinical "Hitra-disease" to hypotonic saline. R. Salte and K. Wold, 3rd EAFP Conference 1987, 3 PP EAFP.

Our preliminary investigations on fish suffering from "Bremnes disease" have disclosed obvious similarities between this disease and "Hitra-disease"; red cell fragility increases compared to healthy controls and there is an activation of the coagulation systems similar to DIC.

It is already known that cell membrane integrity in poikilotherms which routinely experience change in environmental temperature is highly dependent on the fatty acid composition of the diet (Cossins and Lee, 1985; Leray et al., 1986), and membrane lipids are the only structural components of cells known to participate in the temperature adaptation process.

From EPO patent publication No. 0222/96 is known to use unicellar algae of the Chlorella type as feed for artemia. Such uncellar algaes have a high content of n-3 polyunsaturated fatty acids and when artemia is fed with this diet they increase in size and their death rate is reduced.

At present, the content of n-3 fatty acids is not declared for commercially produced fish feed. It is known, however, that fat in Norwegian produced feed mainly originates from marine sources, such as capelin meal and oils containing such acids. The content of EPA/DHA in such lipids will vary depending on season as well as catch area. Still, it is estimated that the percentage of EPA/DHA in feed, normally containing between 17 and 22% (by weight), of fat, will be in the order of 1,5-3% (by weight), and this will amount to about 3-6 Cal %.

Current knowledge shows a preferential incorporation of unsaturated fatty acids into phospholipids at low water temperatures. This selectivity of incorporation is thought to be of importance in restructuring cell membranes during thermal acclimation.

However, an evaluation of the physical properties achieved by this restructuring of the poikilotherm's cell membranes in terms of disease seems to be lacking.

The inventors made an initial assumption that insufficient supply and/or production of unsaturated fatty acids may lead to an impairment of membrane structure and function, and ultimately this may lead to disease, Salte. Thomassen and Wang, Norsk Fiskeoppdrett 1987.

According to the invention they decided to compose a new and improved feed with a high content of n-3 polyunsaturated fatty acids or alternatively to provide an additive especially rich in said n-3 acids which may be added to the feed before use.

The feed is in the form of a mechanical blended mixture made up from a number of raw materials supplying the desirable levels of proteins, lipids and digestible carbohydrates and possibly including vitamins, minerals, adhesives and preservatives, which feed contains from 300-600 parts by wt of protein, from 150-300 parts by wt of digestible carbohydrates and from 100-400 parts by wt of lipids, and where the amount of n-3 fatty acids or acid derivatives such as EPA and DHA will be at least 3.5% and preferably from 4.5%-8.5% by wt but based on the total amount of dry matter.

As feed additive, there is provided fish oil concentrate containing at least 22% by wt, preferably at least 30% by wt, of n-3 polyunsaturated fatty acids or a digestive derivative thereof such as a salt, ester or amide. Other characteristic and essential features of the feed and feed additive will be apparent from the accompanying claims and the description following below.

A pilot experiment was undertaken to decide whether the new feed with a high dietary supply of unsaturated fatty acids improves the physical properties of the cell membranes in farmed salmon held at low water temperatures as expressed by the osmotic resistance of erythrocytes to hypotonic saline and, if so, whether such restructuring of the cell membranes is of potential value in prevention of disease associated with membrane degeneration and dysfunction. Our results show that it is possible to improve by dietary manipulation the physical properties of cell membranes in Atlantic salmon held at low water temperatures, as expressed by the osmotic resistance of red cells to hypotonic saline.

The effects on disease or rather the prevention of disease which is associated with cell membrane dysfunction at low water temperatures are thus demonstrated and this is supposed to be relevant for poikilothermic marine animals in general.

We have surprisingly found that an increase in the fish feed of the available n-3 polyunsaturated fatty acids, especially (All Z) 5, 8, 11, 14, 17 eicosapentaenoic acid (EPA) and (All Z) 4, 7, 10, 13, 16, 19 docosahexaenoic acid to a higher level than what is considered optimal from a dietary or growth point of view, will prevent cold water diseases like those described above.

EXAMPLE

Two hundred clinically healthy Atlantic salmon, Sunndalsøra breed, in their first winter in sea (approximate mean weight 1 kg) were randomly sampled from the stock at AKVAFORSK's sea unit, Aveøy. The fish were put into one pen and fed a semi-moist pellet feed consisting of 47.2% protein silage, 38.5% binder meal and 14.2% of n-3 polyunsaturated acid-concentrate containing 18% 20:5 n-3 and 12% 22:6 n-3, yielding about 36% fat in dry matter.

Ten fish were sampled at zero hours (before the first EPA/DHA feeding), at 12 hours, and at 6, 9 and 16 days after the first feeding. The fish were stunned by a blow to the head, and heparinized blood was sampled by caudal vein puncture.

The method used for measuring cell membrane fragility was a modification of a procedure first used for mammalian erythrocytes (Parpart et al., 1947) and later adapted to nucleated erythrocytes (Kariya, 1950; Sulya et al., 1963; Ezell et al., 1968). A stock solution of sodium chloride in phosphate buffer was prepared which was equivalent to a 9% NaCl solution. Working solutions were prepared from this stock solution by diluting with distilled water; a range of concentrations from 0.30% to 0.9%, in increments of 0.02% NaCl and with a pH of 7.3 were used. The test was performed by adding 50 ul of blood to each 5 ml of the working solutions. The solutions were mixed, incubated at the temperature of the surrounding seawater (recorded at each sampling time) for one hour, and centrifuged at $1.500 \times g$ for 10 minutes. The percentage hemolysis was determined by measuring the optical density at 540 nm, with maximum hemolysis corresponding to the solution having the highest optical density reading.

The results are shown in the accompanying drawing where % NaCl concentration (X-axis) is plotted against % hemolysis (Y-axis) to obtain the cell membrane fragility curves.

The further a curve is to the left hand side of the figure, the stronger are the red cell membranes. From left the first three curves represent: 6 days on EPA/DHA concentrate, 12 hours, 9 days and 16 days (the curves are coinciding); 64 days and zero hour (controls). The curve to the far right is included as a contrast to show the weakness of all membranes of salmon suffering from "Hitra disease".

After 12 hours of feeding at a water temperature of 5.9° C. the osmotic resistance of erythrocytes (red cells) to hypotonic saline had increased significantly ($p<0.05$); at day 6 the increase was even more pronounced.

Nine days after the first feeding the fragility curve had returned to the 12 hour level. The above course of events is indicative of a homeostatically regulated process and it is consistent with the hypothesis of homeoviscous adaptation. It is further compatible with previous reports on the adaptive responses of membranes to temperature and to dietary manipulation (Cossins and Sinensky, 1984). The time required to bring about a significant change in the physical properties of the red cell membrane in this experiment, i.e. about 12 hours, was surprisingly short.

At day 20 the remaining fish were split into 3 groups, each consisting of about 50 fish. Group 1 continued unhandled in the same pen and on the same EPA/DHA-rich feed. Group 2 was netted, sedated in chlorobutanol, individually marked and returned to Group 1. Group 3 was netted, sedated, individually marked, and transported (towed in a small pen) over a distance of several hundred meters after which they were put into a pen which had suffered heavy mortalities due to "Hitra disease" until a week previously. A ten-days treatment with oxolinic acid in this pen (10 mg/kg/fish/day) ended the day before Group 3 fish arrived.

During the first 3 weeks cumulative mortalities reached only 2.0% among the EPA/DHA-fed fish despite repeated sampling stress; corresponding figures for the neighbouring pens were 7.6 and 6.4%, respectively. In Group 3, 8% died immediately in connection with the splitting and transport processes. During the first 3 weeks after splitting, however, 8.7% of the Group 3 fish died compared to 9.1% among controls.

In this connection it must be stressed that the control fish were protected by antibiotics against potential pathogenes for at least a part of this time-period.

In marine fish, polyunsaturated fatty acids of the n-3 series are thought to be essential, and as such should be supplied by the diet. The optimum requirements have as yet only been established for a limited number of species and without taking into account the relationship concerning cell membrane strength at low temperature and related diseases. Most studies have been performed on rainbow trout, on which basis a minimum requirement of about 2-4 cal % has been suggested. T. Watenabe; Comp Biochem Physial Vol 73B, No. 1, 1982.

Taking all this into consideration, a supply of 1,5-3% by weight (i.e. about 2-4 cal %) of EPA/DHA will be below what should be considered as a minimum for the prevention of "Hitra disease" according to our experiments. Also, when conventional dietary far is used, the EPA/DHA fractions are in combination with less saturated fat, cholesterol, etc and this may impair the efficiency of the EPA/DHA fraction compared to the use of this fraction as a specially developed feed additive.

Example of feed compositions:

Feed is normally supplied in three forms;

Dry feed, where the water content is less or equal to 10% by wt.

Soft feed, containing ground wet protein feed to which binder meal is added and containing 30% wt or above of water.

Wet feed, when the feed substance is used whole or churned or ground and to which is added up to 10% binder meal and to which is added vitamins and minerals etc.

These feeds are all made up from proteins (300–600 pts by wt), digestable carbohydrates (150–300 parts by wt) and from lipids (100–400 pts by wt). A typical recipe for salmon dry feed is: 70% bwt Herring fish meal, 21% Extr. wheat meal, 5% capulin oil, 3% Vitamin blend. According to the invention, to all these feeds there should be added extra doses of n-3 unsaturated acids so that the total amount of these acids is at least 3,5% by wt based on total amount of dry matter in the feed. The preferred range will be in the order of 4.5–8.5% based on total amount of dry matter.

Even if there, to our knowledge, have been performed no special feed studies on Atlantic salmon, Arctic char or halibut, the normal fat content of the commercial available feed will be in the order of 10–20% by wt, and this corresponds to an EPA/DHA content of less than 3% by wt even when fish oils are used. According to the invention the fat content may be substantially higher than 25%, for example 30–40%, provided that this is high quality marine oils with a high fraction of the n-3 polyunsalurated fatty acids.

We have found no upper limits to the total amount of the n-3 polyunsaturated acids, but there is a practical limit because of the difficulties to absorb the fat into the feed. By conventional techniques there are difficulties when the fat content exceeds 20–22%. We have solved this problem, however, by providing the feed in a porous form, which will readily absorb the n-3 fatty acids.

Due to the complexity of the marine oils constituents it has been difficult to isolate and purify the individual n-3 polyunsaturated acids such as EPA and DHA in substantial quantities. However, in Norwegian laid open patent application 157307, there is described a process developed by the applicants, which is well suited for the production of EPA/DHA concentrates containing at least 18% by wt of EPA and 12% by wt of DHA in the form of ethyl esters. This process was originally developed for the production of pharmaceutical intermediates but will be suitable also for production of the feed additive according to this invention. The feed and feed additive will be applicable not only for grown salmons and flat fish, but also as start feed for fry and feed for brood stock. Even if it is primarily applicable for typical cold water species such as salmon and halibut, it may also be used for turbot and other warm water species.

An increase of the n-3 fatty acids above the level which is normally used is thus needed, as strongly suggested by the results from our studies, as described above. This is obtained according to the invention by the addition of marine oil concentrates containing increased percentage of polyunsaturated fatty acids of the n-3 series, especially EPA and DHA.

Example of feed additive:

An especially preferred feed additive is highly refined natural fish oil in triglyceride form. The high concentration of EPA and of DHA, together with other important unsaturated fatty acids, and a high content of Vitamin E, make this especially valuable as a feed additive according to the invention.

| Typical Analysis | | | |
|---|---|---|---|
| C 14:0 | 6.5% | C 20:5 | 18.0% |
| C 16:1 | 9.0 | C 20:1 | 7.0% |
| C 16:0 | 16.0% | C 22:6 | 12.0% |
| C 18:2 + 3 | 2.5% | C 22:5 | 2.5% |
| C 18:1 | 15.0% | C 22:1 | 5.0% |
| C 18:0 | 3.0% | C 24:1 | 0.5% |
| | | Others | 3.0% |

One international unit of Vitamin E (1. J.U./G) is added, otherwise the oil is free from preservatives, synthetic anti-oxidants, artificial colours and flavours. When packed in nitrogen blanketed drums and inaccessible to light, the quality will be preserved for at least a year.

The feed additive may be in the form of a EPA/DHA concentrate containing at least 22% by wt, preferably at least 30% by wt or higher of these acids or their derivatives. In addition to a mixture of the n-3 fatty acids, the acids may also be used alone. There is some evidence indicating that pure acids and high concentrations will increase the efficiency of the additive.

We claim:

1. A fish feed for the prophylaxis or treatment of cell membrane dysfunction at low water temperatures in farmed fish, comprising (a) an effective amount, for the prophylaxis or treatment of cell membrane dysfunction at low water temperatures in farmed fish, of at least one n-3 polyunsaturated fatty acid or a dietary acceptable derivative thereof in admixture with (b) one or more conventional fish feed components.

2. The feed as in claim 1, wherein said effective amount is at least 3.5% by weight calculated on the basis of dry matter content of the feed.

3. The feed as in claim 2, wherein said effective amount is from 4.5% to 8.5% by weight calculated on the basis of dry matter weight of the feed.

4. The feed as in claim 1 or claim 2, wherein said n-3 fatty acid is selected from the group consisting of (all-Z)5,8,11,14,17-eicosapentaenoic acid, (all-Z)4,7,10,11,13,16,19-docosahexaenoic acid, dietary acceptable derivatives of said acids, and mixtures thereof.

5. The feed as in claim 4, wherein said dietary acceptable derivatives are selected from the group consisting of salts, esters and amides.

6. A fish feed for the prophylaxis or treatment of cell membrane dysfunction at low water temperatures in farmed fish, comprising a mixture of:
   (a) from 300–600 parts by weight of proteins,
   (b) from 100–400 parts by weight of lipids,
   (c) from 150–350 parts by weight of digestible carbohydrates, and
   (d) at least one n-3 polyunsaturated fatty acid or a dietary acceptable derivative thereof,
   wherein said n-3 -polyunsaturated acid or dietary acceptable derivative thereof is present in an amount of at least 3.5% by weight calculated on the basis of dry matter content of the feed.

7. The feed as in claim 6, wherein said n-3 fatty acid component (b) comprises a mixture of (all-Z)5,8,11,14,17-eicosapentaenoic acid, or a dietary acceptable derivative thereof, and (all-Z)4,7,10,13,16,19-docosahexaneoic acid or dietary acceptable derivative thereof.

8. The feed as in claim 7, wherein said mixture is provided by a fish oil concentrate containing, in total, at least 22% by weight of n-3 -polyunsaturated fatty acids or dietary acceptable derivatives thereof.

9. The feed as in claim 8, wherein said fish oil concentrate comprises at least 17% by weight of (all-Z)5,8,11,14,17-eicosapentaenoic acid and at least 12% by weight of (all-Z)4,7,10,11,13,16,19-docosahexaenoic acid, or of a dietary acceptable derivative of said acids.

10. The feed as in claim 9, which further comprises one or more conventional feed components selected from the group consisting of carriers, adhesives, preservatives, vitamins and minerals.

11. A process for the prevention or treatment of cell membrane dysfunction at low water temperatures in farmed fish, comprising administering to said farmed fish at least one n-3 -polyunsaturated fatty acid or a dietary acceptable derivative thereof in an amount effective to prevent or treat said cell membrane dysfunction.

12. The process as in claim 11, comprising administering a fish oil concentrate comprising (all-Z)5,8,11,14,17-eicosapentaenoic acid and (all-Z)4,7,10,13,16,19-docosahexaneoic acid, or a dietary acceptable derivative of said acids.

* * * * *